United States Patent
Okamura

(10) Patent No.: US 10,086,172 B2
(45) Date of Patent: Oct. 2, 2018

(54) INTRODUCER SHEATH

(71) Applicant: TERUMO KABUSHIKI KAISHA, Shibuya-ku (JP)

(72) Inventor: Ryo Okamura, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 312 days.

(21) Appl. No.: 14/139,075

(22) Filed: Dec. 23, 2013

(65) Prior Publication Data

US 2014/0114290 A1    Apr. 24, 2014

Related U.S. Application Data

(63) Continuation of application No. PCT/JP2012/066433, filed on Jun. 27, 2012.

(30) Foreign Application Priority Data

Jun. 29, 2011    (JP) ................... 2011-144697

(51) Int. Cl.
*A61M 25/06*    (2006.01)
*A61M 29/00*    (2006.01)

(52) U.S. Cl.
CPC .......... *A61M 25/0662* (2013.01); *A61M 29/00* (2013.01); *A61M 2025/0687* (2013.01)

(58) Field of Classification Search
CPC ...... A61M 2025/0687; A61M 25/0662; A61M 29/00
See application file for complete search history.

(56) References Cited

U.S. PATENT DOCUMENTS

| | | | | |
|---|---|---|---|---|
| 5,316,706 A | * | 5/1994 | Muni | A61M 25/0009 264/209.1 |
| 5,614,136 A | * | 3/1997 | Pepin | A61M 25/001 264/149 |
| 5,873,864 A | | 2/1999 | Luther et al. | |
| 6,048,339 A | | 4/2000 | Zirps et al. | |
| 6,890,321 B2 | * | 5/2005 | Luther | A61M 25/0606 604/164.01 |

(Continued)

FOREIGN PATENT DOCUMENTS

CN    201624697 U    11/2010
EP    1 596 898 A    4/2009

(Continued)

OTHER PUBLICATIONS

Partial Supplementary European Search Report dated Feb. 23, 2015, by the European Patent Office in corresponding European Application No. 12805274.3-1506. (7 pages).

(Continued)

*Primary Examiner* — Deanna K Hall
(74) *Attorney, Agent, or Firm* — Buchanan Ingersoll & Rooney PC

(57) ABSTRACT

An introducer sheath is configured to inhibit or prevent a distal section from being curled even when the wall thickness thereof is reduced, an introducer sheath is formed from a sheath tube that has a hollow section into which an elongated body can be inserted, and includes a sheath distal section and a sheath main body section. In the sheath for an introducer, the sheath distal section is formed to be harder than the sheath main body section.

15 Claims, 7 Drawing Sheets

(56) References Cited

U.S. PATENT DOCUMENTS

| | | | |
|---|---|---|---|
| 7,842,024 B2 * | 11/2010 | Burgmeier | A61L 29/14 604/525 |
| 2002/0119264 A1 | 8/2002 | Wang | |
| 2003/0114831 A1 | 6/2003 | Wang et al. | |
| 2003/0139759 A1 | 7/2003 | Schaible et al. | |
| 2005/0043712 A1 | 2/2005 | Devens, Jr. | |
| 2009/0088791 A1 | 4/2009 | Drasler et al. | |
| 2010/0160862 A1 | 6/2010 | Howat et al. | |

FOREIGN PATENT DOCUMENTS

| | | |
|---|---|---|
| JP | 6-335531 A | 12/1994 |
| JP | 8-131552 A | 5/1996 |
| JP | 2004-535950 A | 12/2004 |
| WO | 01/70324 A1 | 9/2001 |
| WO | 02/085440 A2 | 10/2002 |
| WO | 03/061722 A2 | 7/2003 |
| WO | 2004/075952 A2 | 9/2004 |
| WO | 2005/065735 A1 | 7/2005 |
| WO | 2010/075000 A1 | 7/2010 |
| WO | 2010/088239 A1 | 8/2010 |
| WO | 2011/040215 A1 | 4/2011 |
| WO | WO 2013-002286 A1 | 1/2013 |

OTHER PUBLICATIONS

Office Action dated Mar. 23, 2015, by the Chinese Patent Office in corresponding Chinese Patent Application No. 201280032057.9. (7 pages).

International Search Report (PCT/ISA/210) dated Sep. 25, 2012, by the Japanese Patent Office as the International Searching Authority for International Application No. PCT/JP2012/066433.

European Search Report dated Jul. 13, 2015, by the European patent Office in counterpart European Application No. 12805274.3 (16 PGS).

Patent Examination Report dated Nov. 30, 2015, by the Australian Patent Office in corresponding Australian Patent Application No. 2012276660 (5 pages).

Japanese Office Action (Notification of Reasons for Refusal) dated Feb. 9, 2016, by the Japanese Patent Office in corresponding Japanese Patent Application No. 2013-522913 with English translation thereof. (6 pgs).

* cited by examiner

[Fig. 1]
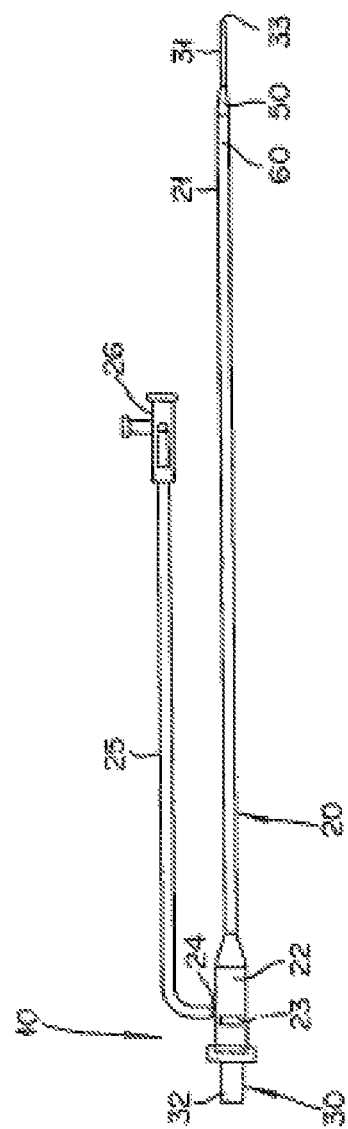

[Fig. 2]
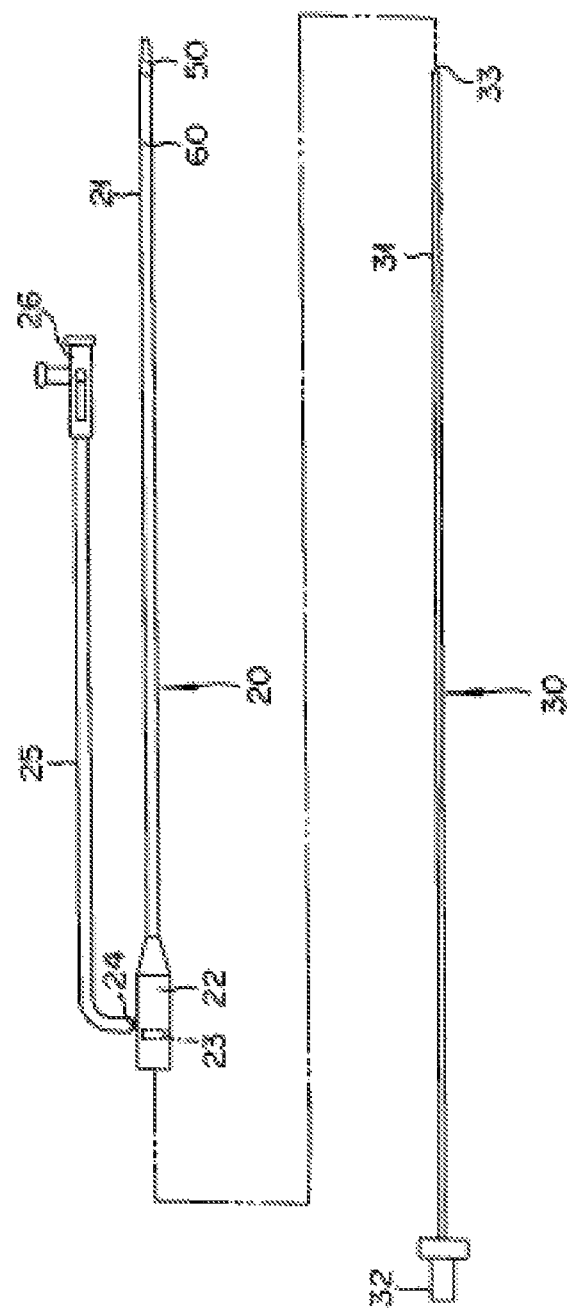

[FIG. 3]
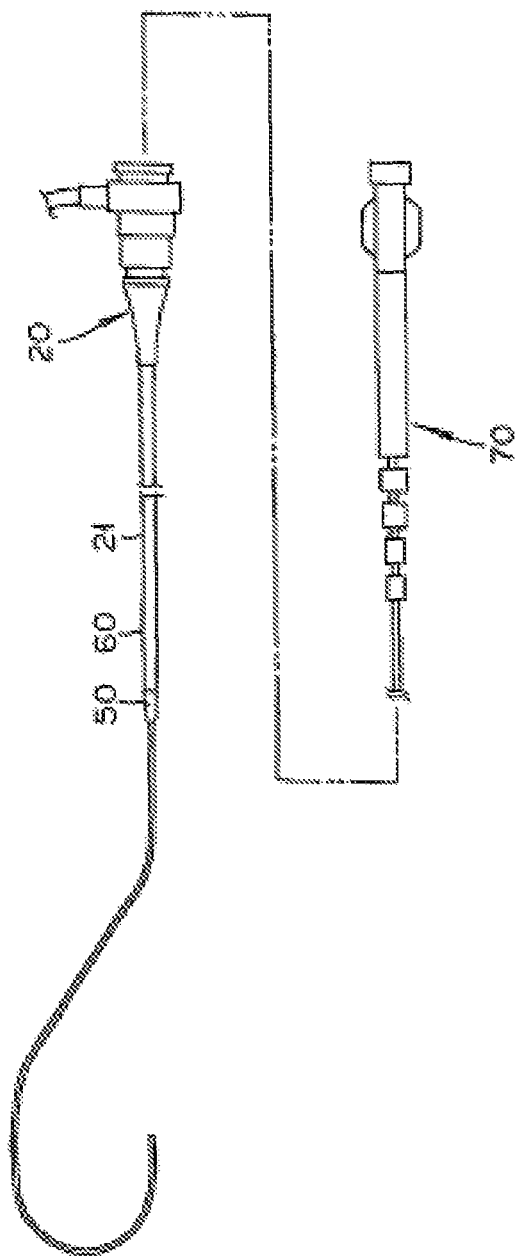

[FIG. 4]
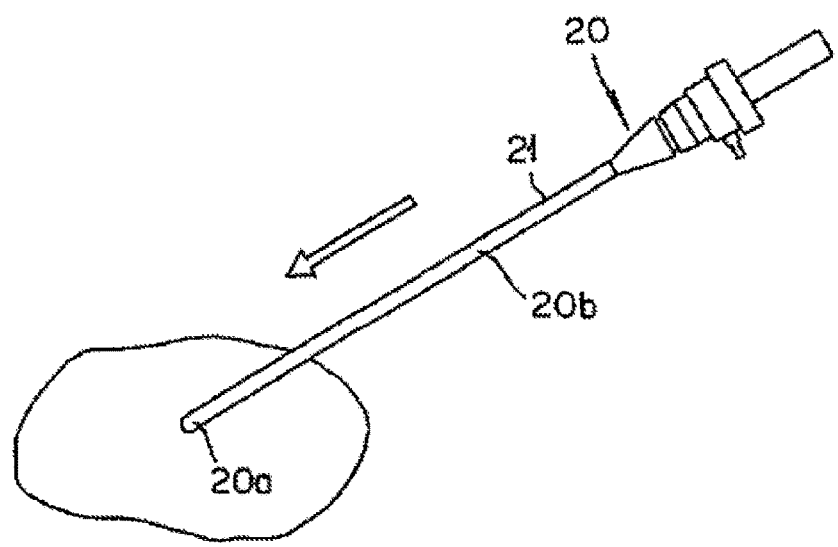
[FIG. 5]
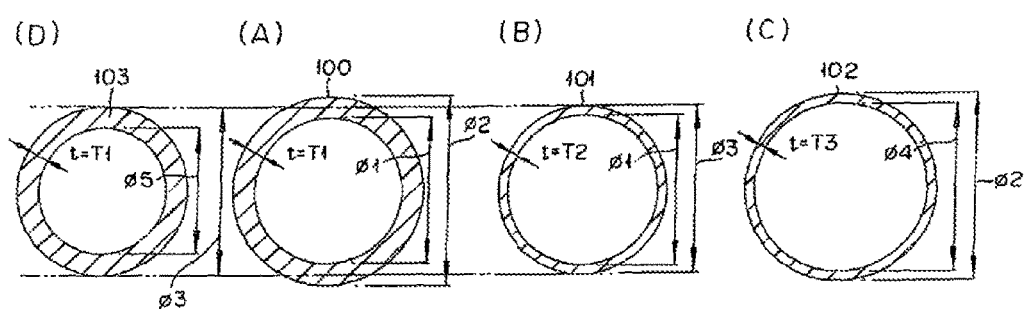

[FIG. 6]
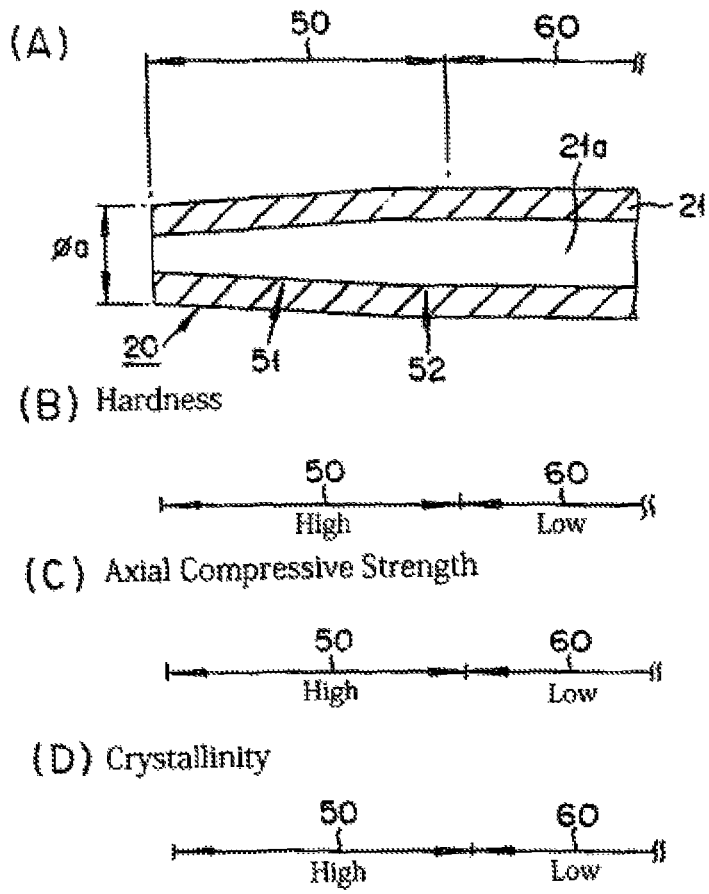
(B) Hardness
(C) Axial Compressive Strength
(D) Crystallinity
[FIG. 7]
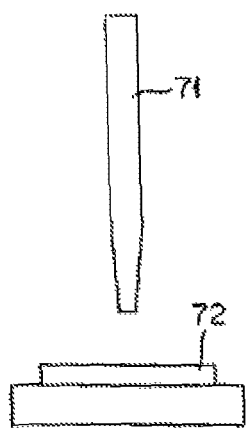

[FIG. 8]
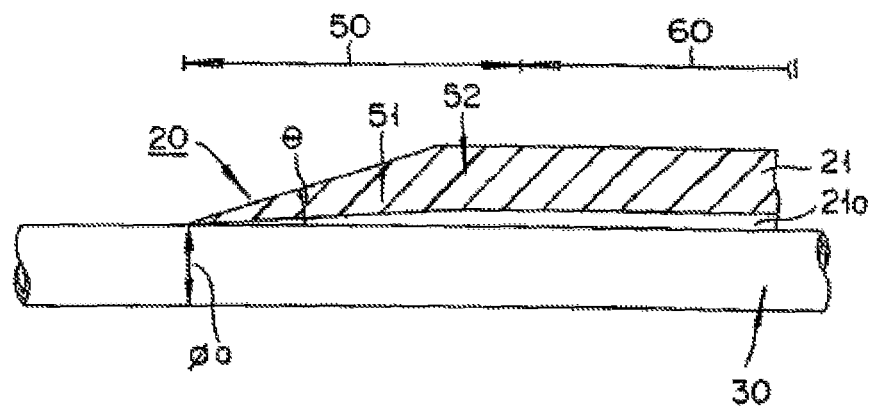
[FIG. 9]
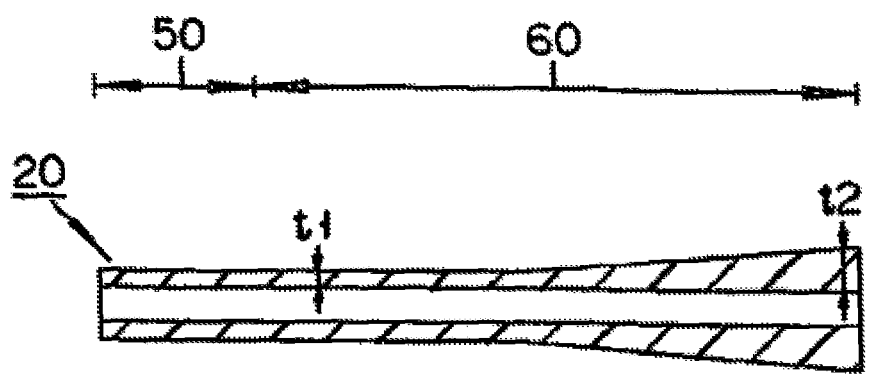

[FIG. 10]
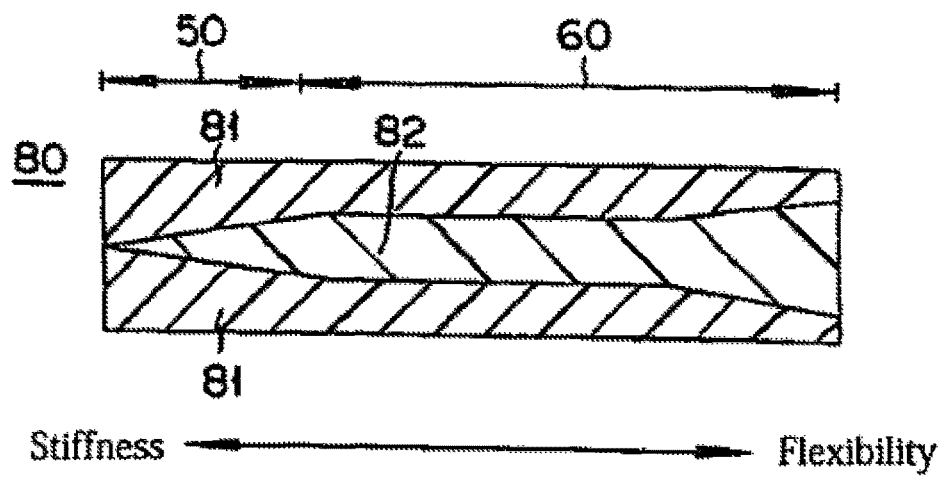
[FIG. 11]
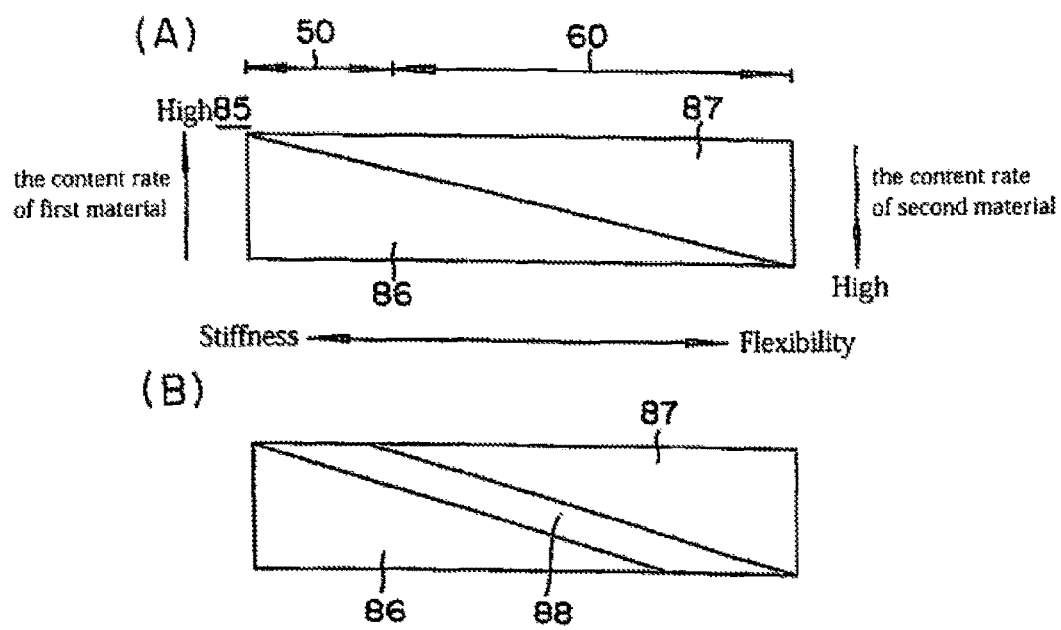

INTRODUCER SHEATH

CROSS REFERENCE TO RELATED APPLICATIONS

This application claims is a continuation of International Application No. PCT/JP2012/066433 filed on Jun. 27, 2012, and claims priority to Japanese Application No. 2011-144697 filed on Jun. 29, 2011, the entire content of both of which is incorporated herein by reference.

TECHNICAL FIELD

The invention generally relates to an introducer sheath.

BACKGROUND DISCUSSION

In recent years, various types of treatments and diagnoses in the medical field have been performed using an elongated and hollow tubular-shaped medical instrument called a catheter. Examples of such treatment methods include directly administering an agent into an affected area by using the elongated configuration of the catheter, push-opening a narrowed section in a lumen of a living body by using a catheter in which a balloon expanded by pressure is attached to a distal end of the catheter, scraping and opening the affected area using a catheter in which a cutter is attached to a distal section of the catheter, and closing arterial aneurysm, bleeding, or feeding vessel sites with a filling material by using the catheter. Other examples also include a treatment method of embedding and placing a tubular-shaped stent which has a mesh-shaped side surface into the lumen of the living body using the catheter so as to maintain an open state of the narrow section in the lumen of the living body. Further, examples include suctioning an excess liquid for a body in the body.

In general, in a case where the treatment, diagnosis, or the like is performed using the catheter, a catheter introducer is used to introduce an introducer sheath into a puncture site formed in an arm or a leg and the catheter or the like is percutaneously inserted into a lesion area such as a blood vessel via a lumen of the sheath for an introducer. Compared to trans femoral intervention (TFI) in which the an introducer sheath is introduced from a foot, trans radial intervention (TRI) in which the an introducer sheath is introduced from the arm has the advantage of facilitating hemostasis, shortened rest time, fewer bleeding complications, and the like for both patients and hospitals.

The introducer sheath is formed from a sheath tube that is a tubular member which has a hollow section into which an elongated body such as the catheter can be inserted. An example is disclosed in Japanese Application Publication No. 8-131552. The introducer sheath includes a distal section that is a distal side during the introduction into the puncture site, and a main body section that is placed on a proximal side of the distal section.

It is preferable that the wall thickness of the introducer sheath be reduced so that the outer diameter of the sheath is decreased or so that an elongated body that has a large outer diameter can be inserted.

When the wall thickness of the introducer sheath is reduced, there is a possibility that the distal section could curl when the introducer sheath is introduced into the puncture site.

Further, even in a case where the wall thickness of the introducer sheath is reduced, it is necessary to ensure the flexibility of the main body section in order to increase the penetrability of the elongated body such as the catheter. By ensuring the flexibility of the main body section, kinking can be inhibited or prevented and resiliency can be obtained to return to an original shape even in the case of the kink.

In prior introducer sheaths, the curling of the distal section is not improved and the flexibility of the main body section is not ensured even when the wall thickness of the main body section is reduced.

SUMMARY

According to one aspect, an introducer sheath comprises: a hollow tubular member open at opposite ends and through which is inserted an elongated body during use of the introducer sheath, wherein the hollow tubular member includes a hollow distal section and a hollow main body section, and with the main body section being positioned proximal of the distal section. The distal section of the tubular member either: i) possesses an axial compressive strength greater than the axial compressive strength of the main body section so that the distal section is harder than the main body section; or ii) possesses a crystallinity greater than the crystallinity of the main body section so that the distal section is harder than the main body section.

According to another aspect, an introducer sheath comprises: a tubular member provided with a hollow section through which an elongated body is freely inserted, with the tubular member including a distal section and main body section, and wherein the main body section is positioned proximal of the distal section, and with the distal section being harder than the main body section.

The introducer sheath is able to inhibit or prevent the distal section from being curled even when the wall thickness of the distal section is reduced, and to provide a introducer sheath that is able to ensure flexibility of the main body section even when the wall thickness of the main body section is reduced.

Another aspect of the disclosure involves an introducer sheath comprising: a tubular member provided with a hollow section through which an elongated body is freely inserted, with the tubular member including a distal section and main body section, and the main body section being formed of a polymer composition containing a crystalline polymer, with the degree of crystallization of the crystalline polymer in the main body section being suppressed.

Even when the wall thickness of the distal section is reduced, it is possible to suppress curling of the distal section when the introducer sheath is introduced into a puncture site since the distal section is harder than the main body section.

It is preferable that the axial compressive strength of the distal section be greater than the axial compressive strength of the main body section. In this case, the distal section is harder than the main body section, and, even when the wall thickness of the distal section is reduced, it is possible to suppress the curling of the distal section when the introducer sheath is introduced into a puncture site.

The crystallinity of the distal section is preferably higher than the crystallinity of the main body section. In this case, the distal section is harder than the main body section, and, even when the wall thickness of the distal section is reduced, it is possible to suppress the curling of the distal section when the introducer sheath is introduced into a puncture site.

It is preferable that the outer diameter of the distal section gradually decreases toward the distal end, and the angle between the outer diameter of the distal section and the axis or axial direction is less than 15 degrees. In this case, the distal angle of the distal section is an acute angle, and it is possible for the curling to unlikely occur during an insertion into a skin hole after an expansion of the skin by a dilator.

The wall thickness of a proximal side of the main body section is preferably larger than the wall thickness of the distal side of the main body section. In this case, resiliency is provided, and the main body section is unlikely to be bent and kinked, and kinking can be inhibited or prevented.

The tubular member is formed of a single layer that is formed of one material, and the distal section can be made harder than the main body section.

It is preferable that the tubular member have a first layer formed of a first material, and a second layer formed of a second material which is softer than the first material, with the thickness of the first layer of the distal section being larger than the thickness of the first layer of the main body section, and the thickness of the second layer of the distal section being smaller than the thickness of the second layer of the main body section. In this case, by changing the thickness of the layer at every site along the longitudinal direction of the introducer sheath, a phased change or inclination from stiffness to flexibility can be given from the distal section toward the main body section. Also, a continuous change or inclination from stiffness to flexibility can be given. Even if the wall thickness of the introducer sheath is relatively thin, curling of the distal section can be suppressed and the insertability into the skin and the blood vessel can be increased by helping to ensure the stiffness of the distal section. Also, the penetrability of a device such as a catheter can be increased by ensuring the flexibility of the main body section. The main body section is unlikely to be bent and kinked, and is likely to be extended even when bent and kinked. Therefore, the main body section is likely to return to an original shape even when the sheath kinks after a puncture.

It is preferable that the tubular member be formed of a mixture of the first material and the second material which is softer than the first material, and the content amount of the first material in the mixture is decreased and the content amount of the second material is increased from the distal side of the distal section toward the proximal side of the main body section. In this case, by changing the content amounts of the first and second materials at every site along the longitudinal direction of the introducer sheath, a continuous change or inclination from stiffness to flexibility can be given from the distal section to the main body section. Also, a phased change or inclination from stiffness to flexibility can be given. Even if the wall thickness of the introducer sheath is thin, the curling of the distal section can be suppressed and the insertability into the skin and the blood vessel can be increased by ensuring the stiffness of the distal section. Also, the penetrability of the device such as the catheter can be increased by helping to ensure the flexibility toward a proximal section of the main body section. The main body section is unlikely to be bent and kinked, and is likely to be extended even when bent and kinked. Therefore, the main body section is likely to return to the original shape even when the sheath kinks after the puncture.

A distal end section of the distal side of the distal section may be formed only of the first material and a proximal end section of proximal side of the main body section may be formed only of the second material.

The introducer sheath disclosed here is configured to ensure appropriate stiffness of the main body section by the stiffness of the crystalline polymer itself and to ensure flexibility of the main body section by suppressing the degree of crystallization of the crystalline polymer. Accordingly, it is possible to obtain the introducer sheath in which the flexibility of the main body section is ensured even when the wall thickness of the main body section is reduced.

It is preferable that the crystalline polymer be polyether ether ketone. In this case, the stiffness strength of the polyether ether ketone is extremely high, and it is possible to obtain the introducer sheath in which the flexibility of the main body section is ensured even when the wall thickness of the main body section is reduced.

It is preferable that the wall thickness of the tubular member be between 0.01 mm and 0.20 mm. In this case, it is possible to obtain the introducer sheath in which the flexibility of the main body section is ensured even when the wall thickness of the main body section is reduced.

BRIEF DESCRIPTION OF DRAWINGS

FIG. 1 is a plan view of an introducer assembly to which an introducer sheath according to an embodiment disclosed here by way of example is applied.

FIG. 2 is an exploded plan view showing the an introducer sheath and a dilator of the introducer assembly.

FIG. 3 is a view showing a state where a catheter is inserted via the introducer sheath that is introduced into a puncture site.

FIG. 4 is a view showing a state where the introducer sheath is introduced into the puncture site.

FIGS. 5(A) and 5(D) are cross-sectional views showing sheaths for introducer whose wall thickness is relatively large, and FIGS. 5(B) and 5(C) are cross-sectional views showing sheaths for introducer whose wall thicknesses are relatively small.

FIG. 6(A) is a cross-sectional view showing the introducer sheath according to the disclosed embodiment, FIG. 6(B) is a schematic view showing a relationship between the hardness (resistance to deformation) of a distal section and the hardness of a main body section of the introducer sheath, FIG. 6(C) is a schematic view showing a relationship between the axial compressive strength of the distal section and the axial compressive strength of the main body section, and FIG. 6(D) is a schematic view showing a relationship between the crystallinity of the distal section and the crystallinity of the main body section.

FIG. 7 is a schematic illustration of a method for measuring the axial compressive strength of the distal section of the introducer sheath.

FIG. 8 is a cross-sectional view showing a sheath distal section.

FIG. 9 is a cross-sectional view showing the introducer sheath in which the kink resistance of the main body section is increased.

FIG. 10 is a cross-sectional view showing a material that is a material which forms a sheath tube and is formed from a plurality of layers which are formed of a different material.

FIGS. 11(A) and 11(B) are schematic views showing the content rates of first and second materials in a mixture of materials which form the sheath tube.

DETAILED DESCRIPTION

Set forth below with reference to the accompanying drawing figures is a detailed description of an embodiment of a sheath for an introducer representing an example of the sheath for an introducer disclosed here. Common features are identified by the same reference numerals throughout and so detailed descriptions of already described features are not repeated. In some cases, dimensional ratios in the drawings are exaggerated and are different from the actual ratios for the convenience of description.

An introducer assembly 10 is a device that ensures an access route into a lumen of a living body. In the description below, the hand operation unit side of the device from which the device is operated will be referred to as the "proximal side," and the side that is inserted into the lumen of the living body will be referred to as the "distal side."

FIG. 1 illustrates an introducer assembly 10 to which is applied an introducer sheath 20 according to an embodiment disclosed here by way of example, FIG. 2 depicts the introducer sheath 20 and a dilator 30 of the introducer assembly 10, FIG. 3 illustrates a catheter 70 inserted via the introducer sheath 20 that is introduced into a puncture site and FIG. 4 shows a state in which the introducer sheath 20 is introduced into the puncture site.

Referring initially to FIGS. 1 and 2, the introducer assembly 10 includes the introducer sheath 20 and the dilator 30. The introducer sheath 20 is comprised of a sheath tube 21, a sheath hub 22 that is attached to the proximal end of the sheath tube 21, and a hemostasis valve 23 that is attached to the proximal end of the sheath hub 22. The dilator 30 is comprised of a dilator tube 31, and a dilator hub 32 that is attached to the proximal end of the dilator tube 31. Referring to FIGS. 3 and 4, the dilator 30 is removed after the introducer sheath 20 is introduced into the puncture site, and an elongated body such as the catheter 70 is percutaneously inserted into a lesion area such as a blood vessel via a lumen of the introducer sheath 20.

After being introduced into the lumen of the living body, the introducer sheath 20 remains in the lumen of the living body. Therein, an elongated body or elongated device, examples of which include the catheter 70, a guide wire, and an embolus material, is inserted into the sheath to be introduced into the lumen of the living body.

The sheath tube 21 is percutaneously introduced into the lumen of the living body. A material constituting the sheath tube 21 will be described later.

A side port 24 that communicates with an inner section of the sheath tube 21 is formed in the sheath hub 22. One end of a tube 25 that is formed of, for example, polyvinyl chloride and has flexibility is liquid-tightly connected to the side port 24. A three-way stopcock 26, for example, is mounted on the other end of the tube 25. A liquid, examples of which include physiological saline, is injected via the tube 25 into the introducer sheath 20 from a port of the three-way stopcock 26.

A material constituting the sheath hub 22 is not particularly limited, but a hard material such as hard resin is suitable. Specific examples of the hard resin include polyolefin such as polyethylene and polypropylene, polyamide, polycarbonate, and polystyrene.

The hemostasis valve 23 is formed from a substantially elliptical membrane-shaped (disk-shaped) elastic member, and is liquid-tightly fixed to the sheath hub 22.

The material constituting the hemostasis valve 23 is not particularly limited, but examples include an elastic member such as silicone rubber, latex rubber, butyl rubber, and isoprene rubber.

The dilator 30 is used to prevent the sheath tube 21 from being bent and kinked, and to expand the diameter of a perforation on the skin when the introducer sheath 20 is inserted into the blood vessel.

The dilator tube 31 is inserted into the sheath tube 21. FIG. 1 shows the distal end 33 of the dilator tube 31 protruding from the distal end of the sheath tube 21. That is, the distal end 33 of the dilator tube 31 protrudes distally beyond the distal end of the sheath tube 21.

Examples of a material constituting the dilator tube 31 can include a polymer material such as polyolefin (for example, polyethylene, polypropylene, polybutene, an ethylene-propylene copolymer, an ethylene-vinyl acetate copolymer, an ionomer, and a mixture of at least two thereof), a polyolefin elastomer, a cross-linked body of polyolefin, polyvinyl chloride, polyamide, a polyamide elastomer, polyester, a polyester elastomer, polyurethane, a polyurethane elastomer, fluorine resin, polycarbonate, polystyrene, polyacetal, polyimide, and polyetherimide, and a mixture thereof.

The dilator hub 32 is detachably held at the sheath hub 22.

The material constituting the dilator hub 32 is not particularly limited, but a hard material such as hard resin is suitable. Specific examples of the hard resin include polyolefin such as polyethylene and polypropylene, polyamide, polycarbonate, and polystyrene.

Referring to FIG. 4, when the introducer sheath 20 is introduced into the puncture site, a distal side 20a is required to be relatively hard to improve insertability into the skin, and a proximal side 20b is required to be relatively flexible to improve device insertability. Further, the proximal side 20b is required to be flexible from the viewpoint of being unlikely to be bent and kinked, being likely to be extended even in the case of bending and kinking, and being likely to return to an original shape even when the sheath kinks or bends after a puncture.

FIGS. 5(A) and 5(D) are cross-sectional views showing sheaths 100 and 103 for an introducer whose wall thickness (t=T1) is relatively large, and FIGS. 5(B) and 5(C) are cross-sectional views showing sheaths 101 and 102 for an introducer whose wall thicknesses (t=T2 and T3) are relatively small.

As shown in FIGS. 5(A) and 5(B), the outer diameter dimension $\phi 3$ can be reduced by, for example, one Fr size ($\phi 2 > \phi 3$) at the same inner diameter dimension $\phi 1$ by reducing the wall thickness (t=T2, T1>T2) of the sheath 101 for introducer. Also, as shown in FIGS. 5(A) and 5(C), the inner diameter dimension $\phi 4$ can be increased ($\phi 4 > \phi 1$) at the same outer diameter dimension $\phi 2$ by reducing the wall thickness (t=T3, T1>T3) of the sheath 102 for introducer. Therefore, the inner diameter dimension $\phi 4$ allows insertion of an elongated body possessing an even larger outer diameter. As shown in FIGS. 5(A) and 5(D), the inner diameter dimension $\phi 5$ is also reduced in size ($\phi 1 > \phi 5$) even when the outer diameter dimension $\phi 3$ is reduced by one Fr size ($\phi 2 > \phi 3$) with the wall thickness (t=T1) of the sheath 103 for introducer being maintained. As a result, only an elongated body possessing a small outer diameter dimension can be inserted.

The range of applications is extended as follows by reducing the wall thickness of the introducer sheath 20. Because the outer diameter of the introducer sheath (7 Fr size introducer sheath) into which a medical device with a 7 Fr size (7 Fr outer diameter) is inserted was larger than the blood vessel diameter (approximately 2.9±0.6 mm) of a radial artery, it was impossible to perform TRI procedure by using the device such as the catheter 70 with a 7 Fr size. Herein, the outer diameter dimension of the introducer sheath can be reduced in size by one Fr (6 Fr size) at the same inner diameter dimension by reducing the wall thickness of the introducer sheath 20. In this manner, it is possible to perform TRI procedure by using the device with a 7 Fr size. The device (medical device) with an outer diameter of 7 Fr size can be inserted into the introducer sheath with an outer diameter of 6 Fr size. In the present specification, such device size-sheath size combination is referred to as "7 in 6."

That is, the introducer sheath expressed as "7 in 6" means the inner diameter of the introducer sheath is sized to receive a device (medical device) having an outer diameter of 7 Fr size, and the outer diameter of the introducer sheath is equivalent to an outer diameter of a known introducer sheath corresponding to 6 Fr size. Thinning the wall thickness of a known 7 Fr introducer sheath makes possible the above-described "7 in 6" introducer sheath. A medical device possessing a 7 Fr outer diameter can be inserted into an introducer sheath expressed as "7 in 6".

The device size-sheath size combination is not limited to "7 in 6," but can be applied to all Frs. For example, all outer diameter sizes can be reduced by one Fr size as "11 in 10," "10 in 9," "9 in 8," "8 in 7," "7 in 6,", "6 in 5," "5 in 4," "4 in 3," and "3 in 2." In the case of "3 in 2," the introducer sheath outer diameter dimension is, for example, approximately ϕ1.39 mm.

In addition, as the sheath outer diameter dimension is reduced by one Fr size, an insertion mark on the human body becomes smaller and the hemostasis time is shortened. In this manner, the hospital stay time is shortened, and a physical burden on a patient and an economic burden on a hospital become lighter.

As described above, the outer diameter dimension can be reduced in size by one Fr at the same inner diameter dimension by reducing the wall thickness of the introducer sheath 20. However, in a case where only the sheath is made thinner, the distal section may curl or buckle, and cannot be used as the sheath. Also, the elastic strength and the stiffness disappear to cause immediate kinking. Examples of the curling of the distal section of the sheath include a case where the material of the sheath distal section extends to be wound around an outer side of the sheath distal section when the introducer sheath is introduced into the puncture site because the wall thickness of the sheath is relatively thin. Also, the buckling of the distal section of the sheath refers to a phenomenon that the sheath causes a deformation in the lateral direction as pressure in the vertical direction is added to the sheath distal section when the introducer sheath is introduced into the puncture site, examples of which include the sheath being bent and kinking into a bellows shape.

The introducer sheath 20 according to an embodiment disclosed here by way of example, which addresses the above-described problem caused when the wall thickness of the introducer sheath is reduced, will be described in detail.

The introducer sheath 20 is generally described with initial reference to FIG. 6(A). The introducer sheath 20 is formed from the sheath tube 21 (constituting a tubular member). The sheath tube 21 has a hollow section 21a into which the elongated body such as the catheter 70 can be inserted. The sheath tube 21 includes a sheath distal section 50 (constituting a distal section), and a sheath main body section 60 (constituting a main body section). The sheath distal section 50 and the sheath main body section 60 are integrally constituted in one-piece by integral molding or the like, and it is preferable that these sections not be bonded by adhesion, welding, or the like. The sheath distal section 50 has a tapering tapered section 51, and a straight section 52 that extends substantially parallel with the axis of the sheath 20. The introducer sheath 20 is formed in such a manner that the sheath distal section 50 is harder than the sheath main body section 60 (refer to FIG. 6(B)).

Even when the wall thickness of the sheath is reduced, it is possible to suppress curling of the sheath distal section 50 when the introducer sheath 20 is introduced into the puncture site since the sheath distal section 50 is harder than the sheath main body section 60.

The sheath distal section 50 being harder than the sheath main body section 60 refers in this embodiment to the axial compressive strength of the sheath distal section 50 being higher (greater) than the axial compressive strength of the sheath main body section 60 (refer to FIG. 6(C)).

As shown in FIGS. 6(B) and 6(C), the mechanical characteristics of the sheath distal section 50 and the sheath main body section 60 are different from each other, but it is preferable that the characteristics be gradually shifted in a boundary region of the two sections. It is preferable that the hardness gradually changes in the boundary section of the sheath distal section 50 and the sheath main body section 60. It is preferable that the axial compressive strength gradually change in the boundary section of the sheath distal section 50 and the sheath main body section 60. It is preferable that the crystallinity gradually changes in the boundary section of the sheath distal section 50 and the sheath main body section 60. Thus, instead of abruptly changing from the hardness/axial compressive strength/crystallinity of one section 50 or 60 to the hardness/axial compressive strength/crystallinity of the other section 60 or 50 at a specific point, the hardness, axial compressive strength and crystallinity characteristics gradually change from one section to the other in an intermediately located boundary section. In this manner, it is possible to not cause or to avoid a rapid change in the mechanical characteristics in the boundary section, and it is possible to suppress kinking when the introducer sheath 20 is introduced into the puncture site.

The material constituting the sheath tube 21 in this case is not limited to a polymer composition containing a crystalline polymer, but a general material can be used. Examples of the material constituting the sheath tube 21 can include a polymer material such as polyolefin (for example, polyethylene, polypropylene, polybutene, an ethylene-propylene copolymer, an ethylene-vinyl acetate copolymer, an ionomer, and a mixture of at least two thereof), a polyolefin elastomer, a cross-linked body of polyolefin, polyvinyl chloride, polyamide, a polyamide elastomer, polyester, a polyester elastomer, polyurethane, a polyurethane elastomer, fluorine resin, polycarbonate, polystyrene, polyacetal, polyimide, and polyetherimide, and a mixture thereof. An ethylene tetrafluoroethylene copolymer (ETFE) can be used suitably.

An evaluation of the compressive strength is performed as follows. FIG. 7 is a schematic view showing a method for measuring the axial compressive strength of the sheath distal section 50.

A processed article 71 in the sheath distal section is cut to 7 cm, and is vertically fixed in a chuck to an Autograph manufactured by Shimadzu Corporation. A cored bar or a dilator that is cut to correspond to the sheath inner diameter is inserted into the sheath tube with an approximately 15 mm gap from the sheath distal section. That is, the distal end of the cored bar/dilator is spaced proximally from the distal end of the article 71 by approximately 15 mm. A urethane sheet 72 is installed below the fixed sheath distal processed article 71 and is vertically moved at a speed of 5 mm/min, and the strength is measured when the distal end of the article 71 is crushed. The laboratory atmosphere is room temperature (RT, approximately 23° C.) and relative humidity (RH, approximately 50%). A similar performance is made with respect to a processed article in the sheath main body section with regard to the axial compressive strength of the sheath main body section.

The curling of the sheath distal section 50 is determined as follows.

First, the urethane sheet is inclined and set at 45 degrees, and punctured with a needle and a wire. There, in a state where the dilator is combined (i.e., the core rod/dilator is inserted into the article 71 as described above to produce an introducer assembly composed of the introducer sheath 20 and the dilator 30 which have been integrated with each other), the pressing is made by the autograph and the presence or absence of the curling of the sheath distal section is determined. That is, the presence or absence of curling is determined by inserting the tip of the article 71 (the introducer assembly in which the introducer sheath 20 is inserted the dilator 30) into the hole in the urethane sheet produced by puncturing with the needle and wire. And the tip of the article 71 is inserted into the hole in the urethane sheet while the sheet is at a 45 degree angle.

Instead of the sheath distal section 50 being harder than the sheath main body section 60 by virtue of varying the axial compressive strength as described above, the sheath distal section 50 being harder than the sheath main body section 60 can also refer to the crystallinity of the sheath distal section 50 being higher than the crystallinity of the sheath main body section 60 (refer to FIG. 6(D)).

Molding of a non-crystallized tube is performed as follows.

In a first molding method, when the polymer composition containing the crystalline polymer is extrusion-molded, quenching is performed in a die to mold the non-crystallized tube. The cylinder molding temperature is approximately between the melting point of the polymer and 150° C. above the melting point of the polymer, and the die temperature is between 50° C. and 300° C.

In a second molding method, the polymer composition containing the crystalline polymer is quenched in a water tank after being extrusion-molded to mold the non-crystallized tube. The cylinder molding temperature is approximately between the melting point of the polymer and 150° C. above the melting point of the polymer, the die temperature is between 100° C. and 300° C., and the water tank temperature is between 0° C. and 80° C.

A relationship between the temperature of polyether ether ketone (PEEK), which is the crystalline polymer, and the crystallinity is as follows. The glass transition point Tg of the PEEK is approximately 145 degrees, and the melting point Tm of the PEEK is approximately 345 degrees. The crystallinity increases when the PEEK is molded at a temperature tens of degrees lower than the melting point Tm from around the melting point Tm. That is, the crystallinity increases when the PEEK is molded within a range of a temperature tens of degrees lower than the melting point Tm from a temperature under the melting point Tm. In general, annealing is performed also at a temperature tens of degrees lower than the melting point Tm. In the first molding method, the molding is performed at a temperature tens of degrees higher than the glass transition point Tg. In this manner, the crystallinity is decreased. In the second molding method, even when the molding is performed at a temperature tens of degrees lower than the melting point Tm, the crystallinity is decreased since the molded tube is quenched by being put into the water tank or the like.

When a shaping process is performed on the sheath distal section 50, a mold is used in which a recess is formed to have an inner surface shape matching the tapered shape of the sheath distal section 50. The mold is heated by a high-frequency power source. The distal end of the sheath tube 21 is pushed into the recess of the mold. Then, the inner surface shape of the recess is transferred to the distal end of the sheath tube 21, and the tapered section 51 with a tapering outer surface is formed in the sheath distal section 50. The crystallinity of the sheath distal section 50 to which heat and pressure are added becomes higher than the crystallinity of the sheath main body section 60 through this shaping process. In a case where the material of the sheath is polyether ether ketone (PEEK), it is preferable that the temperature of the mold (i.e., the mold having the recess that is used to shape the distal end of the sheath tube) be between the glass transition point Tg and 150° C. above the melting point Tm.

The crystallinity of the crystalline polymer can be measured by, for example, X-ray diffraction, a thermal analysis method, a density method, an infrared method, or a nuclear magnetic resonance absorption method.

Even the polymer that has crystallinity is not a 100% crystal, but contains a crystalline area where a main chain and a side chain of a molecule are regularly lined up and a non-crystalline (amorphous) area where a main chain and a side chain are not regularly lined up in each molecular structure. Accordingly, the crystalline polymer may contain at least the crystalline area in the molecular structure, and may contain the crystalline area and the non-crystalline area mixed with each other.

The resin generally used in the introducer sheath is mainly fluorine-based resin such as ethylene tetrafluoroethylene copolymer (ETFE) and FEP, and general-purpose resin such as PE. However, these resins have an insufficient elastic strength, stiffness, and mechanical strength when made thin, and are very difficult to achieve a function as the sheath.

As the material constituting the sheath tube 21 in the case of the introducer sheath disclosed here, engineering plastic and super engineering plastic, which are not used in general as a sheath material, are used. Examples of the plastic used here include polyether ether ketone (PEEK), that has a melting point as high as 340° C. but an extremely high stiffness strength and high stability, polyether ketone (PEK), polyether ketone ketone (PEKK), polyether ether ketone ketone (PEEKK), polyphenylene sulfide (PPS), polyether sulfone (PES), polysulfone (PSF), polyimide (PI), polyetherimide (PEI), amorphous polyarylate (PAR), and super engineering plastic derivatives thereof. Also, there is a case where a fibrous reinforcing material is added so as to increase the mechanical strength. For example, there is a case where glass fiber and carbon fiber, whisker, mica, aramid fiber, acrylic fiber, or polyester fiber is added. Specific examples thereof include FRP, FRTP, GFRP, GFRTP, CFRP, CFRTP, BFRP, BFRTP, KFRP, and KFRTP. In addition, a compound in which these super engineering plastic is made compatible with PTFE, ETFE, or the like is also useful. Also, engineering plastic such as nylon (polyamide) and polycarbonate, polyacetal, polyphenylene ether, and polybutylene terephthalate can be included.

FIG. 8 is a cross-sectional view showing the sheath distal section 50.

Referring to FIG. 8, the introducer sheath 20 is formed in such a manner that the outer diameter φ of the sheath distal section 50 gradually decreases toward the distal end. Preferably, the angle θ between the outer surface of the sheath distal section 50 and the axial direction (axis of the introducer sheath 20) is less than 15 degrees, and more preferably, five degrees.

The distal angle of the sheath distal section 50 is an acute angle, and curling is unlikely to be generated during an insertion into the skin hole after an expansion of the skin by the dilator 30.

It is preferable that the angle of the sheath distal section 50 is 10 degrees or less since the material is thin. For example, in a case where the wall thickness is approximately 70 μm and the sheath distal angle is 15 degrees, the insertion into the skin is difficult, but the insertion into the skin is facilitated in a case where this is five degrees.

FIG. 9 is a cross-sectional view showing the introducer sheath 20 in which the kink resistance of the sheath main body section 60 is increased.

Referring to FIG. 9, it is preferable that the wall thickness t2 of the proximal end portion of the sheath main body section 60 is larger than the wall thickness t1 of the distal end portion of the sheath main body section 60.

In a case where a thin sheath is to be realized using a stiff material, resiliency is lowered when the sheath is bent and kinked in a sheath proximal section. Accordingly, the wall thickness t2 of the proximal end portion of the sheath main body section 60 is made larger than the wall thickness t1 of the distal end portion of the sheath main body section 60, and resiliency is realized. According to the configuration, the sheath main body section 60 is unlikely to be bent and kinked, and so kinking can be inhibited or prevented. Examples of the manufacturing method include withdrawal of molten resin and correction by a mold. Also, it is possible to use not only a single-layered tube formed only of the stiff material, but also a tube formed of multi-layered materials.

In the embodiment illustrated described above, the sheath tube 21 is formed of a single layer that is formed of one material, and the sheath distal section 50 is made harder than the sheath main body section 60 by any of the above-described measures.

FIG. 10 is a cross-sectional view showing the material that is the material which forms the sheath tube 21 and is formed from a plurality of layers which are formed of a different material.

Referring to FIG. 10, a material 80 forming the sheath tube 21 has a first layer 81 that is formed of a first material, and a second layer 82 that is formed of a second material which is softer than the first material. The thickness of the first layer 81 of the sheath distal section 50 is larger (greater) than the thickness of the first layer 81 of the sheath main body section 60, and the thickness of the second layer 82 of the sheath distal section 50 is smaller (less) than the thickness of the second layer 82 of the sheath main body section 60. In the example that is shown, the material forming the sheath tube 21 has a three-layered structure of an outer layer, a middle layer, and an inner layer, which are formed of the stiff material (material that is relatively inflexible or less easily bent) that is the first material, the flexible material that is the second material, and the stiff material that is the first material, respectively.

By changing the thickness of the layer at every site along the longitudinal direction of the introducer sheath 20, the distal side (distal end portion) can be rich or abundant with the stiff material and the proximal side (proximal end portion) can be rich or abundant with the flexible material. In other words, the ratio of the stiff material is higher in the thickness direction of the distal side (distal end portion) than on the proximal side (proximal end portion). In this manner, a phased change or inclination from stiffness to flexibility can be given from the sheath distal section 50 toward the proximal end of the sheath main body section 60. Also, a continuous change or inclination from stiffness to flexibility can be imparted.

According to the material forming the sheath tube in this manner, even for an introducer sheath 20 that is relatively thin, the curling of the sheath distal section 50 can be suppressed and the insertability into the skin and the blood vessel can be increased by ensuring appropriate stiffness of the sheath distal section 50. Also, the penetrability of the device such as the catheter 70 can be increased by ensuring the flexibility toward the proximal section of the sheath main body section 60. The sheath main body section 60 is unlikely to be bent and kinked, and is likely to be extended even when bent and kinked. That is, the sheath main body section 60 is unlikely to be bent and kinked, and can nevertheless extend along the lumen of the sheath main body section 60 even when bent and kinked. The sheath main body section 60 is flexible and thus returns to the original shape even when bent and kinked. Accordingly, there is the advantage of being likely to return to the original shape (kink resiliency) even when the sheath kinks after the puncture.

Referring to FIGS. 11(A) and 11(B), a material 85 forming the sheath tube 21 is a mixture of a first material and a second material, wherein the second material is softer than the first material. The sheath tube 21 is a single-layered tube formed of the mixture. The content rate 86 of the first material in the mixture is decreased and the content rate 87 of the second material is increased from the distal end of the sheath distal section 50 toward the proximal end of the sheath main body section 60. That is, in the illustrated embodiment, the percentage or amount 86 of the first material in the mixture decreases from a maximum at the distal end of the sheath distal section 50 to a minimum at the proximal end of the sheath main body section 60 (i.e., from a maximum at the distal end of the tubular member to a minimum at the proximal end of the tubular member), and the percentage or amount 87 of the second material in the mixture increases from a minimum at the distal end of the sheath distal section 50 to a maximum at the proximal end of the sheath main body section 60 (i.e., from a minimum at the distal end of the tubular member to a maximum at the proximal end of the tubular member). In the example that is shown, the distal side end section of the sheath distal section 50 is formed only of the stiff material that is the first material and the proximal side end section of the sheath main body section 60 is formed only of the flexible material that is the second material.

By changing the content rates (amounts) 86 and 87 of the first and second materials at every site along the longitudinal extent or direction of the introducer sheath 20, the distal end portion can be rich or abundant in the stiff material and the proximal end portion can be rich or abundant in the flexible material. In this manner, a continuous change or inclination from stiffness to flexibility can be given from the sheath distal section 50 toward the proximal end of the sheath main body section 60. Also, a phased change or inclination from stiffness to flexibility can be given. Herein, being rich or abundant in the stiff material shows a state where the content rate of the stiff material is relatively high, and being rich or abundant in the flexible material shows a state where the content rate of the flexible material is relatively high.

Ways in which richness in the stiff material is changed to richness in the flexible material include the ratios of the two materials gradually changing (refer to FIG. 11(A)) and the form of being changed through a state 88 where the two resins are compatible with each other (refer to FIG. 11(B)). The state in which the two resins are compatible with each other refers to the state 88 in which the two resins are the same mixing ratio with each other so that in the compatible state 88, the mixing rate of the first material 86 and the second material 87 is the same everywhere. Specifically, in FIG. 11(A), the content rate 86 of the first material in the mixture is decreased and the content rate 87 of the second material is increased from the distal end of the sheath distal section 50 toward the proximal end of the sheath main body section 60. For example, in a case where the first material and the second material are not mixed with each other (e.g., where the sheath member 20 is formed of two separate members having overlapping portions forming a double-layered tube.), the thickness of a member 86 which is formed of the first material in the material 85 is decreased and the thickness of a member 87 which is formed of the second material in the material 85 is increased from a distal end of the sheath distal section 50 toward a proximal end of the sheath main body section 60 as shown in FIG. 11(A). Thus, "86" in the drawing figures represents the content rate of the first material in the mixture or the first material member, and "87" represents the content of the second material in the mixture or the second material member. Also, in a case where the first material and the second material are mixed with each other in the mixture, the content rate 86 of the first material of the mixture constituting the material 85 is decreased and the content rate 87 of the second material of the mixture constituting the material 85 is increased from the distal end of the sheath distal section 50 toward the proximal end of the sheath main body section 60 as shown in FIG. 11(A). Also, in FIG. 11(B), the content rate 86 of the first material in the mixture is decreased and the content rate 87 of the second material is increased through the state 88 where the two resins are compatible with each other from the distal side of the sheath distal section 50 toward the proximal side of the sheath main body section 60. That is, in the state 88, the content rate 86 of the first material in the mixture and the content rate 87 of the second material in the mixture is the same. In other words, as shown in FIG. 11(B), the thickness of the member 86 formed of the first material in the material 85 is decreased and the thickness of the member 87 formed of the second material in the material 85 is increased from the distal end of the sheath distal section 50 toward the proximal end of the sheath main body section 60, and, on a boundary surface of the member 86 formed of the first material and the member 87 formed of the second material, a layer that has a constant thickness in a state where the two members are compatible with each other (i.e., a state in which the member 86 formed of the first material and the member 87 formed of the second material are mixed) is formed. An adjustment of the content rates 86 and 87 can be performed by a method using extrusion molding technology.

According to the sheath tube-forming material, even if the wall thickness of the introducer sheath 20 is relatively thin, the curling of the sheath distal section 50 can be suppressed and the insertability into the skin and the blood vessel can be increased by helping to ensure appropriate stiffness of the sheath distal section 50. Also, the penetrability of the device such as the catheter 70 can be increased by helping to ensure the flexibility toward the proximal section of the sheath main body section 60. The sheath main body section 60 is unlikely to be bent and kinked, and is likely to be extended even when bent and kinked. Accordingly, there is the advantage of being likely to return to the original shape (kink resiliency) even when the sheath kinks after the puncture.

In the introducer sheath 20, the following configuration can be adopted to help ensure the flexibility of the sheath main body section 60 even when the wall thickness of the sheath main body section is reduced.

In other words, the introducer sheath 20 is formed from the sheath tube 21 (corresponding to the tubular member) that has the hollow section 21a into which the elongated body such as the catheter 70 is inserted, and has the sheath distal section 50 and the sheath main body section 60. The sheath main body section 60 is formed of the polymer composition containing the crystalline polymer and in which the degree of crystallization of the crystalline polymer is suppressed.

It is possible to ensure the stiffness of the sheath main body section 60 by the stiffness of the crystalline polymer itself and to ensure the flexibility of the sheath main body section 60 by suppressing the degree of crystallization of the crystalline polymer. Accordingly, it is possible to obtain the introducer sheath 20 in which the wall thickness of the sheath main body section 60 is reduced, yet appropriate flexibility of the sheath main body section 60 is ensured.

The above-described first molding method and the second molding method having the quenching process may be applied to the suppression of the crystallization. Also, an agent that suppresses crystallization may be added instead of the quenching process or in addition to the quenching process.

The suppressed degree of crystallization of the crystalline polymer that is suppressed is changed by the tube diameter, wall thickness, length, and the like, and thus is not definitely determined but the optimal degree of crystallization is selected through trial and error. Accordingly, the suppressed degree of crystallization does not necessarily have to be specified by using the crystallinity.

Polyether ether ketone (PEEK) can be suitably used in the crystalline polymer. The stiffness strength is extremely high and the stability is high.

The wall thickness of the sheath tube 21 is between 0.01 mm and 0.20 mm, preferably between 0.03 mm and 0.15 mm. The inner diameter of the sheath tube 21 is between 0.10 mm and 5.00 mm.

Hereinabove, the introducer sheath 20 disclosed here has been described based on embodiments disclosed by way of example. However, the present invention is not limited in this regard.

For example, a shape that has a three-layered structure is shown in FIG. 10 as the material 80 which forms the sheath tube 21. However, a double-layered structure or a four-layered or a five-layered structure may be used.

Also, according to the example that is shown, the distal side end section of the sheath distal section 50 is formed only of the stiff material that is the first material and the proximal side end section of the sheath main body section 60 is formed only of the flexible material that is the second material (FIG. 11). However, the respective end sections may contain the first and second materials.

The detailed description above describes an introducer sheath that receives an elongated medical device such as a catheter. The disclosure here is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. An introducer sheath comprising:
a hollow tubular member open at opposite ends and through which is inserted an elongated body during use of the introducer sheath, the hollow tubular member including a hollow distal section and a hollow main body section, the main body section being positioned proximal of the distal section, and wherein a proximal end of the main body section is configured to be in communication with a sheath hub and a distal end of the distal section is configured to be inserted into a lumen in a living body, the distal section of the tubular member possessing an axial compressive strength greater than the axial compressive strength of the main body section and a crystallinity greater than the crystallinity of the main body section so that the distal section is harder than the main body section;

the hollow tubular member including a boundary section of the distal section and the main body section, the boundary section having a constant wall thickness and wherein the axial compressive strength and the crystallinity gradually change in the boundary section;

the distal section of the tubular member including an outer surface and an inner surface, the outer surface and the inner surface tapering in a narrowing manner toward the distal end of the distal section; and the main body section possessing a wall thickness and the distal section possessing a wall thickness, the wall thickness of a proximal end portion of the main body section being greater than the wall thickness of a distal end portion of the main body section.

2. The introducer sheath according to claim 1, wherein an entirety of the tubular member is no more than a single layer formed of only one material.

3. The introducer sheath according to claim 1, wherein a length of the main body section is greater than a length of the distal section.

4. The introducer sheath according to claim 1, wherein the outer surface tapering forms an angle of less than 15 degrees with a central axis of the distal section.

5. The introducer sheath according to claim 1, wherein a wall thickness of the tubular member is between 0.01 mm and 0.20 mm.

6. An introducer sheath comprising:

a hollow tubular member open at opposite ends and through which is inserted an elongated body during use of the introducer sheath, the hollow tubular member including a hollow distal section and a hollow main body section, the main body section being positioned proximal of the distal section, and wherein a proximal end of the main body section is configured to be in communication with a sheath hub and a distal end of the distal section is configured to be inserted into a lumen in a living body, the distal section of the tubular member possessing an axial compressive strength greater than the axial compressive strength of the main body section and a crystallinity greater than the crystallinity of the main body section so that the distal section is harder than the main body section;

the distal section of the tubular member including one portion in which an outer surface of the tubular member tapers in a narrowing manner toward the distal end of the distal section and an other portion in which the outer surface of the tubular member is parallel to a central axis of the sheath, and wherein the other portion in which the outer surface is parallel to the central axis is distal of the one portion in which the outer surface of the tubular member tapers in the narrowing manner; and the distal section of the hollow tubular member possessing a boundary section, the boundary section having a constant wall thickness, and wherein the axial compressive strength and the crystallinity gradually change in the boundary section.

7. The introducer sheath according to claim 6, wherein the main body section possesses a wall thickness and the distal section possesses a wall thickness, the wall thickness of a proximal end portion of the main body section being greater than the wall thickness of a distal end portion of the main body section.

8. The introducer sheath according to claim 6, wherein an entirety of the tubular member is no more than a single layer formed of only one material.

9. The introducer sheath according to claim 6, wherein the outer surface of the tubular member tapers in the narrowing manner forms an angle of less than 15 degrees with the central axis of the distal section.

10. The introducer sheath according to claim 6, wherein a wall thickness of the tubular member is between 0.01 mm and 0.20 mm.

11. An introducer sheath comprising:

a hollow tubular member open at opposite ends and through which is inserted an elongated body during use of the introducer sheath, the hollow tubular member including a hollow distal section and a hollow main body section, the main body section being positioned proximal of the distal section, and wherein a proximal end of the main body section is configured to be in communication with a sheath hub and a distal end of the distal section is configured to be inserted into a lumen in a living body, the distal section of the tubular member possessing an axial compressive strength greater than the axial compressive strength of the main body section and a crystallinity greater than the crystallinity of the main body section so that the distal section is harder than the main body section;

the hollow tubular member including a boundary section of the distal section and the main body section, the boundary section having a constant wall thickness, and wherein the axial compressive strength and the crystallinity gradually change in the boundary section; and the distal section of the tubular member including an outer surface and an inner surface, the outer surface and the inner surface tapering in a narrowing manner toward the distal end of the distal section.

12. The introducer sheath according to claim 11, wherein a length of the main body section is greater than a length of the distal section.

13. The introducer sheath according to claim 11, wherein the outer surface tapering forms an angle of less than 15 degrees with a central axis of the distal section.

14. The introducer sheath according to claim 11, wherein a wall thickness of the tubular member is between 0.01 mm and 0.20 mm.

15. The introducer sheath according to claim 11, wherein an entirety of the tubular member is no more than a single layer formed of only one material.

* * * * *